US007518010B2

(12) United States Patent
Atanasov et al.

(10) Patent No.: US 7,518,010 B2
(45) Date of Patent: Apr. 14, 2009

(54) BIOMIMETIC SYSTEMS CONSISTING OF LIPID MEMBRANES BOUND TO AN ELECTRICALLY CONDUCTING SUBSTRATE

(75) Inventors: Vladimir Atanasov, Mainz (DE); Ingo Köper, Mainz (DE); Wolfgang Knoll, Mainz (DE); Stefan Schiller, Oestrich-Winkel (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 128 days.

(21) Appl. No.: 11/448,127

(22) Filed: Jun. 7, 2006

(65) Prior Publication Data

US 2006/0292637 A1 Dec. 28, 2006

Related U.S. Application Data

(60) Provisional application No. 60/689,056, filed on Jun. 10, 2005.

(51) Int. Cl.
*C07F 7/04* (2006.01)
*C07F 7/08* (2006.01)

(52) U.S. Cl. ....................................... 556/445; 556/446

(58) Field of Classification Search ................. 556/445, 556/446

See application file for complete search history.

(56) References Cited

OTHER PUBLICATIONS

Yamauchi, K., Hihara, M., Kinoshita, M., "Synthesis of 1,2-Di-O-alkyl-sn-glycero-3-phosphatidylcholine Using 2-Methoxyethoxymethyl and 2-(Trimethylsilyl)ethoxymethyl Protective Groups.", Bull. Chem. Soc. Jpn., 1987, 60, 2169-2172.*

Silverman R., The Organic Chemistry of Drug Design and Drug Action, 1992, Academic Press Inc., p. 19.*

* cited by examiner

*Primary Examiner*—Shaojia Anna Jiang
*Assistant Examiner*—Jennifer Y Cho
(74) *Attorney, Agent, or Firm*—Rothwell, Figg, Ernst & Manbeck, P.C.

(57) ABSTRACT

The invention concerns lipids functionalized with a terminal C═C double bond which can be transformed into an anchor group for binding to a substrate surface. The invention further concerns lipids comprising such an anchor group for binding to a substrate surface. The invention also concerns self-assembled monolayers of lipids on substrates, in particular on silicon oxide substrates. The lipids and the lipid monolayers or bilayers containing these lipids can be used to produce biomimetic supported membrane systems. These membrane systems can be directly anchored on silicon microelectronic devices. After the optional incorporation of functional molecules such as membrane-associated proteins such systems can used for applications such as model systems for examining biological membranes, screening methods, sensors and bioelectronic devices such as biocomputers.

11 Claims, 9 Drawing Sheets

Figure 1:
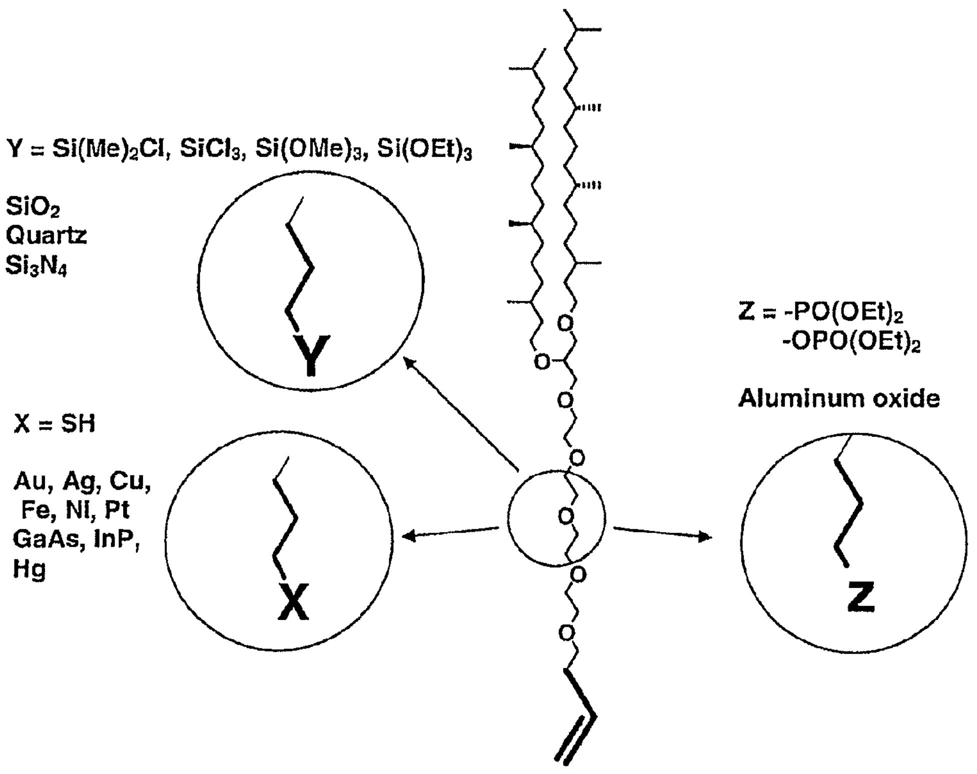

Scheme 1:
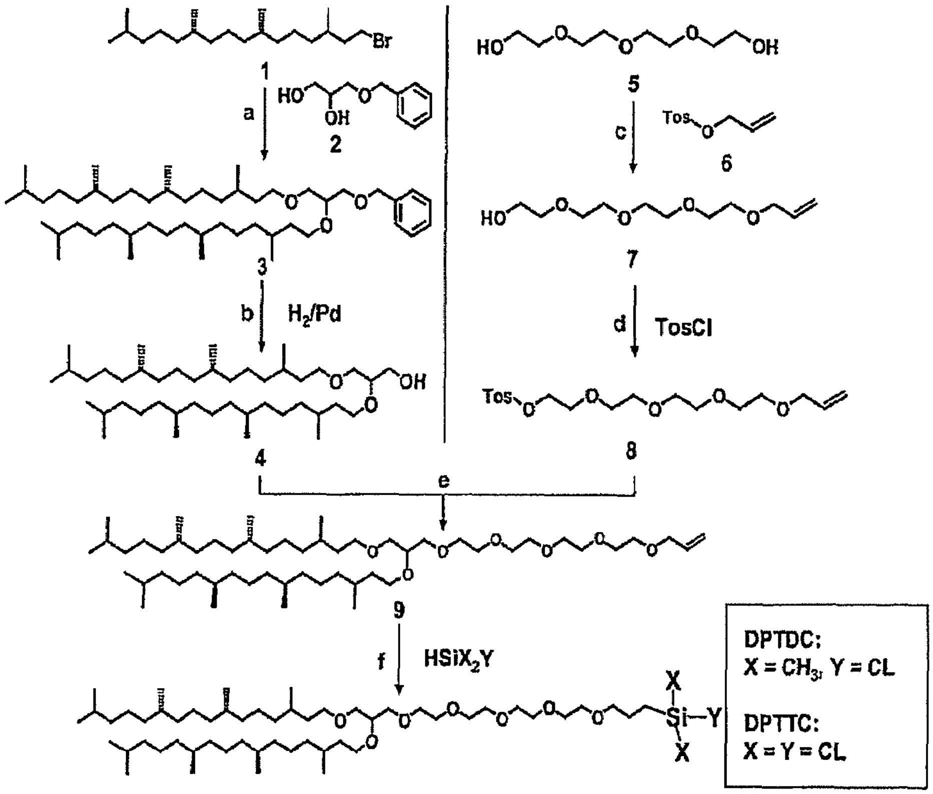

A

A

A

BIOMIMETIC SYSTEMS CONSISTING OF LIPID MEMBRANES BOUND TO AN ELECTRICALLY CONDUCTING SUBSTRATE

CROSS REFERENCE TO RELATED APPLICATION

This application claims priority from U.S. Provisional Application No. 60/689,056 filed Jun. 10, 2005.

The invention concerns lipids functionalized with a terminal C═C double bond which can be transformed into an anchor group for binding to a substrate surface. The invention further concerns lipids comprising such an anchor group for binding to a substrate surface. The invention also concerns self-assembled monolayers of lipids on substrates, in particular on silicon oxide substrates. The lipids and the lipid monolayers or bilayers containing these lipids can be used to produce biomimetic supported membrane systems. These membrane systems can be directly anchored on silicon microelectronic devices. After the optional incorporation of functional molecules such as membrane-associated proteins such systems can used for applications such as model systems for examining biological membranes, screening methods, sensors and bioelectronic devices such as biocomputers.

The rapid progress in the elucidation of biological and medical problems has become impeded by limitations in various fields of analysis which impact not only the field of deciphering the genome of entire organisms (genomics) and the field of proteomics which concerns the verification of the code-function relationships between genome and proteome. Also research on cell-cell interactions and membrane proteins depends to an increasing extent on powerful model systems since they can often only be analysed in a native environment under difficult conditions e.g. using methods such as the patch-clamp technique which are not suitable for wide-scale use (standard analyses and measuring systems). An application of biological model membrane systems which does not necessarily primarily depend on their strict electrical properties but rather on their fluidity and chemical properties is the investigation of the processes described above with regard to their influence on cell-cell interactions and neuro (degenerative) cell changes which are also manifested as modified glycolipid structures on the cell surface (Kolter, Sandhoff, Angew. Chem. Int. Ed. 1999, 38, 1532-1568) or are indicated by the occurrence of changed glycopeptide structures (e.g. in the case of mucins which play an important role in cell interactions (Schiller, S., "Diplomarbeit", Mainz, 1998)).

The search for biomimetic systems which enable the investigation of such systems or their use in analytics makes high demands on the model system that is used. A basic requirement is the greatest possible agreement between the natural prototype and the biomimetic model which has to be able to imitate the natural prototype with regard to the properties that are important for the problem in question.

One of the most important biomimetic systems consists of a lipid bilayer similar to the biological membrane which is applied to an electrically conductive planar substrate. Such a system enables the investigation of membrane-associated biomolecules (e.g. $H^+$-ATPase, cytochrome oxidase, ion channels etc.) which are associated with electrical processes or are controlled by them and are therefore used in biosensor systems and in drug screening.

A large number of applications, their biophysical properties and the diverse chemical compositions with regard to the parts of the molecule that support the membrane and variations in the lipid part (from saturated to unsaturated alkyl chains of different chain length in a monomeric, dimeric or multimeric form which can additionally be provided with hydrophobic side groups and can contain various polar head groups which bind them) and their binding to the aforementioned tethering group which is usually polar are described in Ringsdorf et al., "Angew. Chem. Int. Ed.", 1988, 27, 113-158; Lang, et al., Langmuir, 1994, 10, 197; Sackmann, Science, 1996, 271, 43-48; Guidelli et al., J. Electroanal. Chem., 2001, 504, 1-28 and Knoll et al., Mol. Biotechnol., 2000, 74, 137-158.

The functional binding of the lipid membrane to a solid substrate via a flexible polar (hydrophilic) intermediate part is an approach that has been popular for years (Sackmann, see above) and has the following advantages: Firstly it achieves a robust binding of the sensitive lipid bilayer to the solid substrate which, due to its planarity, enables a number of sensitive electrical and surface-analytical methods to be used and also uncouples the membrane from the surface. The uncoupling from the surface suppresses the hydrophobic interaction which occurs on metal surfaces and which is negative for the membrane and increases the cytosol-like volume between the membrane and substrate surface which is of fundamental importance especially for volume-dependent transport processes as well as for generating fluid membranes.

The measuring methods that can be used for membrane systems comprise in the case of electrical methods for example impedance spectroscopy (IS), voltammetry and other potentiometric and amperometric methods such as chrono-coulometry. Methods for analysing surfaces comprise a number of methods, many of which require planar metal films as a proximal layer before modification with the system to be analysed. They often allow an analysis down to submolecular orders of magnitude which can only be achieved by such solid body supported membranes. These include for example surface plasmon resonance spectroscopy (OPR, SPR or SPS) for determining the layer thickness (refractive index) of compounds applied to the substrate (e.g. Au or Ag films). However, a large number of other measuring methods some of which are very sensitive can be used to characterize the described system. These include methods such as ellipsometry, fluorescence methods, internal reflectometry, light scattering methods, X-ray or neutron scattering, surface acoustic methods, utilization of thermal effects (changes in the temperature or heat flow), measurement of masses or changes in density which can for example be determined with a quartz microbalance, measurement of changes in the membrane phase, radioimmunoassays or enzyme-linked assays.

Realization of a model system which allows the application of the said methods and, on the other hand, meets the requirements for a functional biological model membrane having the necessary properties is a problem which makes very high demands on the molecular properties of the membrane components, their surface binding, the molecules which surround them, the properties and quality of the surface and the measuring methods that are to be used.

Numerous examples of supported membrane systems are known from the prior art. For example membrane systems based on thiol-modified oligopeptides and thiol lipopeptides can be used (see e.g. Bunjes et al., Langmuir, 1997, 13, 6188-6194; Naumann et al., Bioelectrochem. Bioenerg. 1997, 42, 241-247; Schmidt et al., Biosensors. Bioelectron. 1998, 13, 585-591; Naumann et al., Biosens. Bioelectron. 1999, 14, 651-662 and WO 96/18645 and WO 99/20649). Peggion et al., Langmuir, 2001, 17, 6585-6592 also describe oligopeptides as membrane-supporting components that are provided with polar triethylene glycol side chains and form a hydrophilic monolayer.

Membrane systems hydrophilically supported by polyethylene glycol are described by Lang et al., Langmuir, 1994, 10, 197-210, Heyse et al., Biochem.Biophys. Acta 1998, 85507, 319-338, EP-A-0 441 120 and EP-A-0 637 384. Another membrane system supported by a short oligoethylene glycol chain which has cholesterol as a hydrophobic domain is described by Williams et al., Langmuir 1997, 13, 751-757 and Jenkins et al., Langmuir, 1998,14, 4657.

Other membrane systems are described by Cornell et al., Nature 1997, 387, 580-583, Raguse et al., Langmuir 1998, 14, 648-659, Krishna et al., Langmuir 2001, 17, 4858-4866 and in WO 89/01159, WO 90/02327, WO 94/07593, WO 97/01092, U.S. Pat. No. 5,753,093 and U.S. Pat. No. 5,783,054. The components used to build-up the membrane are composed of various monophytanyl/monophytanoyl-oligoethylene glycol thiols/disulfides, polar lateral spacer molecules and a membrane-spanning thiolipid. Functionalization molecules such as gramicidin can be incorporated into the membrane. After treating a gold surface with an ethanolic solution of the individual components, the membrane is generated in situ by rinsing with buffer.

The concept of tethered bilayer lipid membranes (tBLMs), where the proximal part of the bilayer membrane is covalently attached to a surface via a spacer unit, has been shown to provide membrane systems with good electrical properties as well as with an increased stability (Braach-Maksvytis and Raguse 2000; Naumann and others 2003a; Raguse and others 1998; Schiller and others 2003). The advantage of using a spacer between substrate and bilayer is the fact that this construct provides an ionic reservoir underneath the membrane and avoids direct contact of embedded membrane proteins with the substrate. Previous assemblies often could not provide sufficiently good electrical sealing properties, an essential criterion for the study of ion transport processes mediated by membrane proteins. Recently, a system with good electrical sealing properties has been developed. Due to a high electrical resistance of the membrane, several membrane proteins were successfully incorporated and characterized in a functional form (Naumann and others 2002; Naumann and others 2003a; Naumann and others 2003b; Vitovic and others 2004).

Especially for biosensing applications, it is interesting to combine the biological system of a membrane, which provides good electrical sealing properties, with a (micro-) electronic read-out system. These electronic systems are mostly based on silicon technology. For example, the simplest gate structure of a non-metallized field-effect transistor for operation in electrolytes consists of a thin layer of silicon oxide.

For the production of the tethered bilayer lipid membranes known in the prior art, lipid molecules are used showing a terminal functional tethering group, e.g. OH, $NH_2$, SH. However, the kind of functional group limits the respective lipid molecule disadvantageously to a particular substrate material, e.g. a metal surface, due to its chemical binding properties.

It was therefore an object of the invention to provide a compound, in particular a lipid precursor which is not limited in advance to a particular substrate material due the linking chemistry of particular functional groups. An adjustable anchor should be provided that gives opportunity for utilizing a large variety of substrates and immobilization techniques.

A further aspect of the invention was the provision of a membrane system being able to form insulating biometric lipid bilayer membranes on silicon oxide surfaces in order to be able to use all advantages of semiconductor industries.

This object is achieved by providing a compound, in particular a lipid precursor, comprising a terminal C═C double bond that can be functionalized to be assembled in a monolayer on various substrates such as metal and oxide surfaces. These "universal" lipid precursors comprise a central moiety derived from a compound having at least two functionalities and preferably 3 or 4 functionalities. The central moiety can for example be an organic group having 3-10 C-atoms which contains hydroxy, diol or/and amino groups as functionalities. Preferred functionalities are hydroxy groups. Other residues that are defined in the following can be bound to these functionalities, e.g. by means of ether bonds, thioether bonds, ester bonds or/and amide bonds. Preferred examples of a central moiety according to the invention are glycerol, 1-amino-propane-2,3-diol,2-amino-2-hydroxymethyl -1,3-propanediol(Tris), amino acids such as serine, threonine, lysine etc., polar compounds with thiol functionalities such as dimercaptosuccinic acid, sugar alcohols such as mesoerythritol, threitol etc, sphingosins and similar glycerol deriviatives, tri- to pentaamines etc. Glycerol is a particular preferred central moiety.

At least one saturated or unsaturated hydrocarbon or acyl residue having a chain length of 10-22 C-atoms which can optionally be substituted by one or more side groups, e.g. $C_1$-$C_4$ alkyl groups and in particular methyl groups is bound to the functionalities of the central moiety. Preferably at least two such hydrocarbon or acyl residues, e.g. 2 or 3 of them are bound to the central moiety. In addition, a spacer residue comprising a $[(CH_2)_mO]_n$ group, wherein m and n are independently integers $\geqq 1$, a linker group and a terminal C═C double bond, is bound to the central moiety.

m is preferably from 1-10, more preferably from 1-5, even more preferred m is 1 or 3 and most preferably m is 2.

n is preferably from 1-20, more preferably from 1-10, even more preferably from 1-5 and most preferred n is 4.

The linker group is a saturated or unsaturated, branched or unbranched, substituted or unsubstituted hydrocarbon having $\geqq 1$ C atoms. Preferably, the linker group shows 1-10 C atoms, more preferably 1-5 C-atoms and most preferably 1-3 C-atoms.

The terminal C═C double bond can be substituted or unsubstituted. If the terminal C═C double bond is substituted, substituents which increase the nucleophilic character of the C═C double bond or stabilize an intermediate during a radical addition are preferred. Any such substitutents known to the person skilled in the art can be used. Any substituents can be in cis or trans position.

In an especially preferred embodiment of the present invention the C═C double bond is unsubstituted.

The terminal C═C double bond is further accessible for an addition reaction of any compound which can be added to a C═C double bond known to the person skilled in the art. Hereinafter such a compound is called "addition agent". Electrophilic addition agents and addition agents which are able to form radicals are preferred. "Addition reaction" according to the invention specifies the addition of an addition agent to the terminal C═C double bond by electrophilic addition or radical addition. Addition agents which result after the addition reaction in ethylthioles, ethylchlorosilanes, ethylalkoxysilanes and ethylphosphonic groups are preferred (FIG. 1). A preferred addition agent is for example $HSiX_2Y$ with X and Y independently $C_1$-$C_3$ alkyl, $C_1$-$C_3$ alkoxy, Br or Cl. In an especially preferred embodiment of the invention X is $CH_3$, Cl, $OCH_3$ or $OC_2H_5$ and Y is Cl, $OCH_3$ or $OCH_2CH_3$.

Another aspect of the present invention is a process for the preparation of a compound comprising a residue selected from the group consisting of ethylthioles, ethylchlorosilanes, ethylalkoxysilanes and ethylphosphonic groups, wherein a compound according to the invention, in particular a lipid precursor, is reacted with an addition agent at the terminal C═C double bond.

According to the invention, compounds comprising an ethylthiol after the addition of an addition agent to the terminal C═C double bond preferably bind to substrates comprising a metal surface such as Au, Ag, Cu, Fe, Ni, Pt, GaAs, InP and Hg.

In another embodiment of the invention compounds comprising an ethylphosphonic group after the addition of an addition agent to the terminal C═C double bond preferably bind to substrates comprising an aluminium oxide surface.

In an especially preferred embodiment compounds comprising an ethylchlorosilane or ethylalkoxysilane after the addition of an addition agent to the terminal C═C double bond bind to $SiO_x$ with $0<x\leqq 5$, $Si_3N_4$ or quartz surfaces. $SiO_2$ surfaces are most preferred.

A further aspect of the invention are compounds that have been functionalized to comprise a terminal silane containing tethering group. These compounds can be obtained by reacting a compound comprising a terminal C═C double bond according to the invention as described above.

Therefore the compounds comprise a central moiety derived from a compound having at least two functionalities and preferably 3 or 4 functionalities. The central moiety can for example be an organic group having 3-10 C-atoms which contains hydroxy, thiol or/and amino groups as functionalities. Preferred functionalities are hydroxy groups. Other residues that are defined in the following can be bound to these functionalities, e.g. by means of ether bonds, thioether bonds, ester bonds, amine bonds or/and amide bonds. Preferred examples of a central moiety according to the invention are glycerol, 1-amino-propane-2,3-diol,2-amino-2-hydroxymetnyl-1,3-propanediol(Tris), amino acids such as serine, threonine, lysine etc., polar compounds with thiol functionalities such as dimercaptosuccinic acid, sugar alcohols such as mesoerythritol, threitol etc, sphingosins and similar glycerol derivatives, tri- to pentaamines etc. Glycerol is a particular preferred central moiety.

At least one saturated or unsaturated hydrocarbon or acyl residue having a chain length of 10-22 C-atoms which can optionally be substituted by one or more side groups, e.g. $C_1$-$C_4$ alkyl groups and in particular methyl groups is bound to the functionalities of the central moiety. Preferably at least two such hydrocarbon or acyl residues, e.g. 2 or 3 of them are bound to the central moiety. In addition, a residue comprising a $[(CH_2)_mO]_n$ group, wherein m and n are independently integers $\geqq 1$, a linker group and tethering group, wherein the tethering group comprises a silane group, is bound to the central moiety. m is preferably from 1-10, more preferably m is 3 and most preferably m is 2.

n is preferably from 1-20, more preferably from 1-10, even more preferably from 1-5 and most preferred n is 4.

The linker group is selected from the group consisting of saturated or unsaturated, branched or unbranched, substituted or unsubstituted hydrocarbons having $\geqq 1$ C atoms, alkylsilanes, arylsilanes and siloxanes. Preferably, the linker group shows 1-10 C atoms, more preferably 1-5 C-atoms and most preferably 1-3 C-atoms.

In a preferred embodiment the tethering group comprising a silane is a chlorosilane or an alkoxysilane. Preferably the tethering group comprises a silane group —$SiR^1R^2R^3$ with $R^1$, $R^2$ and $R^3$ independently selected from the group consisting of saturated or unsaturated, branched or unbranched, substituted or unsubstituted C1 to C10 hydrocarbons, —Br, —Cl, —$OR^6$, alkylsilanes, aryisilanes, silicoles and siloxanes, wherein at least one of $R^1$, $R^2$ and $R^3$ is selected from the group consisting of —Br, —Cl, —$OR^6$ and wherein $R^6$ is a saturated or unsaturated, substituted or unsubstituted C1 to C10 hydrocarbon. Preferably $R^6$ is $CH_3$ or $(CH_2)_pCH_3$ with p being an integer from 1 to 9. p is preferably 1 or 2.

Another aspect of the invention are compounds of the general formulae (Ia) or (Ib)

(Ia)

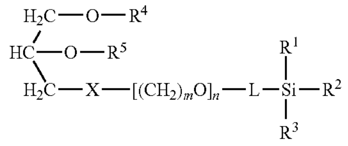

(Ib)

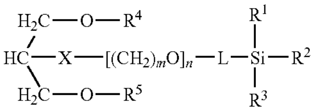

in which $R^1$, $R^2$ and $R^3$ are independently selected from the group consisting of saturated or unsaturated, branched or unbranched, substituted or unsubstituted C1 to C10 hydrocarbons, —Br, —Cl, —$OR^6$, alkylsilanes, arylsilanes, silicoles and siloxanes, wherein at least one of $R^1$, $R^2$ and $R^3$ is selected from the group consisting of —Br, —Cl, —$OR^6$ and wherein $R^6$ is a saturated or unsaturated, substituted or unsubstituted C1 to C10 hydrocarbon, and at least one of $R^4$ and $R^5$ independently denotes a saturated or unsaturated hydrocarbon residue or an acyl residue having a chain length of 10-30 C atoms, preferably 10-22 C atoms, which can optionally be substituted by one or several side groups and/or labelling groups, in particular fluorescent groups, and if only one of $R^4$ and $R^5$ denotes a residue as defined above the other is hydrogen, a $C_1$-$C_9$ hydrocarbon residue or a residue comprising a phospholipid, carboxyl, carbonyl, SO, $SO_2$, amide, amino or thiol group with or without a $C_1$-$C_9$ hydrocarbon residue, and n and m are independently integers $\geqq 1$, and L is a linker group selected from the group consisting of saturated or unsaturated, branched or unbranched, substituted or unsubstituted hydrocarbons having $\geqq 1$ C atoms, alkylsilanes, arylsilanes and siloxanes, and X is a connecting group.

These compounds can be obtained by reacting a compound comprising a terminal C═C double bond according to the invention as described above.

In this connection the compounds (Ia) or (Ib) are 1,2 sn as well as 2,3 sn lipids according to the relevant stereochemical nomenclature for lipids (sn).

In a preferred embodiment, the —$SiR^1R^2R^3$ moiety is selected from chlorosilanes and alkoxylsilanes. In an especially preferred embodiment the —$SiR^1R^2R^3$ moiety is selected from silanes with $R^1$, $R^2$ and $R^3$ independently selected from the group consisting of saturated or unsaturated, branched or unbranched, substituted or unsubstituted C1 to C10 hydrocarbons, —Br, —Cl, —$OR^6$, alkylsilanes, arylsilanes, silicoles and siloxanes, wherein at least one of $R^1$, $R^2$ and $R^3$ is selected from the group consisting of —Br, —Cl, —$OR^6$ and wherein $R^6$ is a saturated or unsaturated, substituted or unsubstituted C1 to C10 hydrocarbon.

$R^6$ is preferably $CH_3$ or $(CH_2)_pCH_3$, p being an integer from 1 to 9, preferably 1 or 2.

In an especially preferred embodiment the —$SiR^1R^2R^3$ group is selected from the group consisting of —$SiCl_3$, —$SiR^7Cl_2$, —$SiR^7_2Cl$, —$Si(OR^6)_3$, —$SiR^7_2(OR^6)$ and —$SiR^7(OR^6)_2$, wherein $R^6$ and $R^7$ are independently saturated or unsaturated, branched or unbranched, substituted or unsubstituted C1 to C10 hydrocarbons. —$Si(Me)_2Cl$, —$SiCl_3$, —$Si(OMe)_3$ and —$Si(OEt)_3$ are most preferred.

At least one of $R^4$ and $R^5$ is a saturated or unsaturated hydrocarbon or acyl residue which can substituted by one or more methyl groups. $R^4$ and $R^5$ are particularly preferably such hydrocarbon or acyl residues. The chain length of $R^4$ and $R^5$ is preferably 12-20 C atoms and particularly preferably 13-18 C atoms. Examples of suitable hydrocarbon and acyl residues are phytanyl, phytanoyl, lauryl, lauroyl, tridecanyl, tridecanoyl, myristyl, myristoyl, pentadecanyl, pentadecanoyl, palmityl, palmitoyl, oleyl, oleoyl, linoleyl, linoleoyl, arachidonoyl, docosahexaenyl, docosahexaenoyl etc. Hydrocarbon residues are particularly preferred which are bound to the central moiety via an ether group, such as phytanyl.

$R^4$ and $R^5$ can optionally be substituted by one or several side groups and/or labelling groups. Any labelling group known to the person skilled in the art is suitable. Labelling groups generating any kind of optical signal, luminescent groups, phosphorescent groups, radioactive groups and/or dye particles are preferred. In an especially preferred embodiment the labelling group is a fluorescent group. $R^4$ and $R^5$ can be substituted by one kind of labelling group or by a combination of different labelling groups.

Compounds of the general formulae (Ia) and (Ib) comprising labelled residues, in particular comprising labelled $R^4$ and $R^5$, can be utilized to determine the amount of these compounds coupled to a subsrate surface or to determine the rate of such a coupling reaction. After being coupled labelled compounds (I) can be utilized further to determine the ratio of these compounds and any other kind of molecules which are close to the substrate surface, such as spacer molecules. In another embodiment of the invention labelled compounds (I) can be utilized to determine energy transfer processes between molecules.

n and m are independently integers from 1-20. n is preferably an integer from 2-20 and especially preferred from 2-5. Most preferred n is 4. m is preferably from 2-5, especially preferred 3 and especially preferred 2. Tetraethylene glycol (m=2 and n=4) is particularly preferred.

The connecting group X is preferably selected from O, S or NR in which R represents H or a $C_1$-$C_4$ alkyl residue. X particularly preferably represents O.

The linker group is a saturated or unsaturated, branched or unbranched, substituted or unsubstituted hydrocarbon having $\geqq 1$ C atoms. Preferably, the linker group shows 1-10 C atoms, more preferably 1-5 C-atoms and most preferably 1-3 C-atoms.

The compounds (I) according to the invention are characterized in that they contain two unpolar lipid groups which are bound to a central moiety component, e.g. a D-glycerol component, via an ether or ester bond. The central moiety binds a residue comprising $[(CH_2)_mO]_n$ group, a linker group and a tethering group comprising a silane on its third functionality, e.g. on a hydroxy group, which is preferably also bound via an ether group. m and n are as defined above. The structure of the compounds according to the invention make them less sensitive to hydrolysis which is very advantageous for long-term applications.

The compounds of the general formulae (Ia) and (Ib) are preferably glycerol derivatives containing in particular 2 hydrocarbon or/and acyl residues and a residue for anchoring to a substrate which residue contains an oligoethylene oxide group having for example 1-10 ethylene oxide units, a linker group comprising for example a $C_3$ hydrocarbon and a tethering group comprising a silane.

Especially preferred compounds according to the present invention have two phytanyl chains connected to the tetra (ethylene glycol) tethered spacer via a glycerol unit. Phytanyl chains were chosen as hydrophobic tails instead of alkyl chains because of their low phase-transition temperature and their influence on the density and stability of biological membranes (Braach-Maksvytis and Raguse 2000; Raguse and others 2000). Furthermore, the 2,3-di-O-phytanyl-sn-glycerol unit contains only ether linkages to prevent hydrolytic cleavage (Mathai and others 2001). This moiety is known to form stable biomembranes under the extreme living conditions (e.g. high temperatures) of extremophiles or archaea (Woese and Fox 1977).

Thus, in a particularly preferred embodiment the compound (I) is selected from 2,3-di-O-phytanyl-sn-glycerol-1-tetraethylene glycol-(3-dichloropropyl-silane)lipid ethers (DPTTC), 2,3-di-O-phytanoyl-sn-glycerol-1-tetraethylene glycol-(3-chloro-dimethylpropyl-silane) lipid ethers (DPTDC) corresponding to 1,2- and 1,3-diphytanyl or diphytanoyl derivatives and optical isomers thereof. It is also possible to select another central moiety for the phytanyl groups instead of the glycerol components such as Tris[2-amino-2-hydroxymethyl-1,3-propane diol] which carries an additional polar hydroxyl group or which is able to receive a third phytanyl group.

The compounds I can be anchored a substrate surface by means of the silane comprising tethering group according to the invention. Preferably the anchoring process on a silicon oxide surface is a self-assembly process. The anchoring reaction itself is preferably a covalent binding between the lipid and the substrate. Preferably, it is a covalent binding between the lipid and a substrate by a condensation reaction of a silane anchor group, preferably a monosilane anchor group with hydroxyl groups available on a surface, preferably a silicon oxide surface.

The immobilization of compound (I) on a $SiO_x$ surface is carried out by immersing the substrate into a dilute solution (0,1-100 mM, more preferably 1-50 mM and even more preferred 2-40 mM) of compound (I). Any substance able to quench co-produced HCl or to promote the reaction such as $Et_3N$ may be added.

In the case of immobilizing compounds like DPTTC a thin water layer adsorbed to the substrate is required. The commonly assumed mechanism for a trichloropropyl-silane anchor group like in DPTTC consists of three distinct phases: 1) the trichlorosilane groups are hydrolyzed by the water layer on the substrate surface; 2) the chains are then bound via hydrogen bonds to the surface and to their neighbors; 3) this (unstable) situation is followed by water elimination leading to a network in which each lipid is linked to the surface and to the neighbors (see FIG. 2) (Silberzan and others 1991). In contrast, in the case of compounds like DPTDC, the covalent binding between the lipid and the substrate occurs after a condensation reaction of the monochlorosilane anchor group with the hydroxyl groups available on the silicon-oxide surface.

Spacer molecules can also be bound to the substrate surface, i.e. molecules having a tethering group comprising a silane as defined above and optionally a hydrophilic group in order to dilute the molecules of compounds (I).

In a preferred embodiment of the invention the spacer molecules are of the general formula $SiR^8R^9R^{10}R^{11}$, wherein $R^8$, $R^9$, $R^{10}$ and $R^{11}$ are independently Cl, —$OR^{12}$, wherein $R^{12}$ is a saturated or unsaturated, substituted or unsubstituted, branched or unbranched C1 to C10 hydrocarbon, or wherein at least one of $R^8$, $R^9$, $R^{10}$ and $R^{11}$ is a residue comprising a $[(CH_2)_m]_n$ group, wherein m and n are independently integers ≧1. m is preferably form 1-10, more preferably m is 2. n is preferably from 1-20, more preferably form 1-10 and most preferably n is 4.

The molar ratio of molecules of compounds (I) to spacer molecules is preferably in a range of 100:0.05 to 0.05:100, particularly preferably in a range of 0.1:100 to 100:1 and most preferably of 15:100 to 70:1. Of course pure tethering lipid layers can also be used. The ratio can be determined by measuring the amount of labelled compounds (I).

Another aspect of the invention is the supported biomimetic membrane comprising a lipid layer containing at least one compound of the general formulae (Ia) or (Ib) as a silane comprising tethering lipid for anchoring to a substrate, in particular a silicone oxide substrate. The lipid layer may comprise a monolayer or, if additional mobile lipids are present, a bilayer.

The substrate preferably has an electrically conductive surface. Preferably the substrate has an oxide surface, in particular a $SiO_x$ surface with 0<x≦5. An even more preferred substrate surface comprises $SiO_2$.

A thin oxide layer is preferred, as it has a capacitance which ensures that the measured impedance is dominated by the smaller capacitance of the bilayer in a series (Purrucker and others (2001)). In a preferred embodiment of the invention doped silicone wafers are used, in particular boron doped silicone wafers. High-doping is favourable because it increases the threshold voltage of the electron inversion layer which acts as an interfering capacitance in the EIS experiments. According to the invention, the silicone wafers are not oxidized but retain their native oxide layers.

Prior to use Si wafers are preferably cleaned thoroughly to increase the surface coverage of OH-groups on the surface. After a surface cleaning of the substrate, the water contact angle is below 15°, more preferably below 10°. The thickness of the oxide layer is preferably 50±10 Å, more preferably 30±10 Å and most preferably 15±5 Å. The RMS roughness is preferably 5.0±1.0 Å, more preferably 3.0±1.0 Å and most preferably 2.0±0.5 Å (from a 5 μm×5 μm area). Silicon wafers which are not further oxidized but retain their native silicon oxide layer are especially preferred.

A monolayer containing compounds of the general formulae (Ia) or (Ib) is perferably hydrophobic.

A supported lipid bilayer can be formed from a monolayer containing compounds of the general formulae (Ia) or (Ib) by adding mobile lipids for example by vesicle fusion. Examples of suitable mobile lipids are phospholipids such as 1,2-di-O-phytanyl-sn-glycero-3-phosphocholine (DphyPC), 1,2-di-O-phytanoyl-sn-glycerophosphocholine, 1,2-di-O-phytanyl-sn-glycerophosphoethanolamine, 1,2-di-O-phytanoyl-sn-glycero-phosphoethanolamine, corresponding 1,2- or 2,3-diphytanyl or diphytanoyl derivatives and mixtures of several of the said compounds or other phospholipids such as egg phosphatidylcholine, DMPC (dimyristoylphosphatidylcholine), DMPE (dimyristoylphosphatidylethanolamine), lecithins and non-phosphorous-containing lipids in a saturated and unsaturated form, provided with identically or differently substituted or non-substituted alkyl chains having preferably 8-22 carbon atoms, in particular with two phytanyl or/and phytanoyl groups which are bound to glycerol by means of ether or/and ester bonds, glycolipids, quarternary ammonium compounds having two $C_1$-$C_4$ alkyl groups and two $C_8$-$C_{18}$ alkyl chains, tertiary amines having two $C_8$-$C_{18}$ alkyl chains and one $C_1$-$C_4$ alkyl chain or a hydrogen atom instead of the $C_1$-$C_4$ alkyl chain, steroids or chemically similar compounds which can be derived from the cholestane structure or isoprenoids as well as lipid mixtures consisting of the said compounds where the lipids can optionally contain polar head groups such as hydroxyl, carboxyl, phosphoric acid ester and derivatives thereof, sulfur oxide derivatives having various oxidation stages of the sulfur and naturally occurring groups such as cholines, ethanolamines, inositols, glycerols, aminoglycerols (in sphingosines) and amino acids and neutral, cationic or anionic forms or derivatives thereof.

The lipid bilayer can also be prepared by LB (Langmuir-Blodgett) transfer of lipid layers, spontaneous bilayer formation, by dilution of for example an ethanolic lipid solution with water or buffer solution or by reverse osmosis and dilution of vesicular solutions.

Another advantage of the supported membrane according to the invention is its simple structure since it can be composed of a monolayer with only a single compound (Ia) or (Ib). It is not necessary to use membrane-spanning lipids which are complicated to synthesize and hence expensive.

The supported lipid bilayer membranes according to the invention have excellent electrical properties. Hence they can have a capacitance of 300 to 1000 nF/cm$^2$, preferably of 500 to 1000 nF/cm$^2$ and even more preferred 750 to 950 nF/cm$^2$.

The resistance is preferably at least 0.1 MΩ·cm$^2$, particularly preferably at least 0.2 MΩ·cm$^2$, for example in the range of 0.2-0.8 MΩ·cm$^2$ or in the range of 0.4-2.5 MΩ·cm$^2$.

Functional molecules can be incorporated into the lipid membrane such as proteins, e.g. membrane-associated proteins, such as $H^+$ ATPases, cytochrome oxidases, ion channels etc. which are associated with electrical processes, other membrane proteins, light-dependent proteins such as bacteriorhodopsin, antibiotics, membrane receptors and ligands e.g. peptides or proteins or other structures containing carbohydrate or/and lipid, or structures composed of heterocycles or combinations thereof.

In a preferred embodiment of the invention the functional molecules are selected from proteins, antibiotics, signal recognition molecules, messenger substances, porines, ion channels, membrane-changing substances such as narcotics, carriers, ligands, receptors, peptides, glycolipids and heterocyclic compounds.

One use of artificial membrane systems is the ability to study functional membrane proteins in a quasi-natural environment. Especially for the investigation of ion transport phenomena the electrical sealing properties of the membranes are important. In this respect, the systems presented according to the invention offer a significant advantage compared to other supported membrane systems.

The supported membranes according to the invention can be used for a large number of applications for example in biosensors and to screen for active substances e.g. to identify or/and characterize pharmacologically active substances. Furthermore the supported membranes can be used to analyse biomolecules such as membrane-associated biomolecules selected from proteins, antibiotics etc. In addition the membranes can be used for electrotechnical applications in particular as electrical insulating materials due to their high resistance and their effective charge separation. They can be used for example in bioelectromechanical micro and nano devices (Bio-MEMS/NEMS) to electrically insulate or embed macroscopic or/and molecular electrical components and for molecular wires (Aviram and Rathner, Chem. Phys. Let. 1974, 29, 257), especially because they have a thickness in a molecular order of magnitude. Moreover, due to their compartmentation capability, the membranes are also able to serve as systems which can for example provide the system components for an interface in biomechanical applications in the field of ATP-dependent electric motors such as e.g. myosin, kinesin and dynein (Taylor et al., Nanotechnology, 1999, 10, 237-243) especially when they are combined with ATP-generating membrane systems or other functional systems e.g. light-dependent proteins such as bacteriorhodopsin.

In an especially preferred embodiment of the present invention membrane system according to the invention is coupled to a silicon oxide surface which offers a direct way to combine the biological system of a membrane to the micro-electronics world of silicon technology, in particular a (micro-) electronic read-out system.

In a further preferred embodiment of the present invention the membrane is anchored directly on a silicon microelectronic device. For example, the simplest gate structure of a non-metallized field-effect transistor for operation in electrolytes consists of a thin layer of silicon oxide. In a especially preferred embodiment the membrane is directly anchored on a chip or on microelectrode array. In an especially preferred embodiment of the invention the membrane is anchored on the gate of a field effect transisitor.

The invention is further elucidated by the following figures and example.

Figure captions

Scheme 1

Synthesis of DPTDC and DPTTC: phytanbromid 1 was synthesized from phytol according to reference(Ishiwatari and others 2002; Schouten and others 1991), a) (±)-3-Benzyloxy-1,2-propanediol 2 (1 equiv), NaH (3.1 equiv), phytanbromid 1 (3 equiv), THF, 40° C., 6 d, 86%; b) this step was carried out according to a procedure described elsewhere (Schiller and others 2003); c) tetraethylene glycol 5 (2 equiv), allyl p-toluenesulfonate 6 (1 equiv), NaH (3 equiv), THF, 45° C., 3 d, 76%; d) p-toluenesulfonyl chloride (2 equiv), NaH (1.5 equiv), TEA (1 equiv), THF, 30° C., 2 d, 77%; e) 4 (1 equiv), 8 (1 equiv), NaH (1.2 equiv), THF, 40° C., 2 d, 62%; f) X=$CH_3$, Y=Cl (DPTDC): dimethylchlorosilane, $H_2PtCl_6$-catalyst, Ar, RT, 6 h, 75%; X=Y=Cl (DPTTC): trichlorosilane, $H_2PdCl_6$-catalyst, Ar, RT, 3 h, 88%.

FIG. 1

Schematic representation of the compound comprising a terminal C=C double bond usable as universal lipid precursor.

FIG. 2

Schematic representation of the arrangement of the DPTTC and DPhyPC molecules forming a tBLM. The picture is somewhat idealized. The packing of the tethered self-assembled monolayers (SAM) is most probably less dense.

FIG. 3

Advancing water contact angles of substrates treated for different lengths of time with DPTTC (circles) and DPTDC (squares) for different assembly times. The lines are guides to the eye.

FIG. 4

Figure 4:
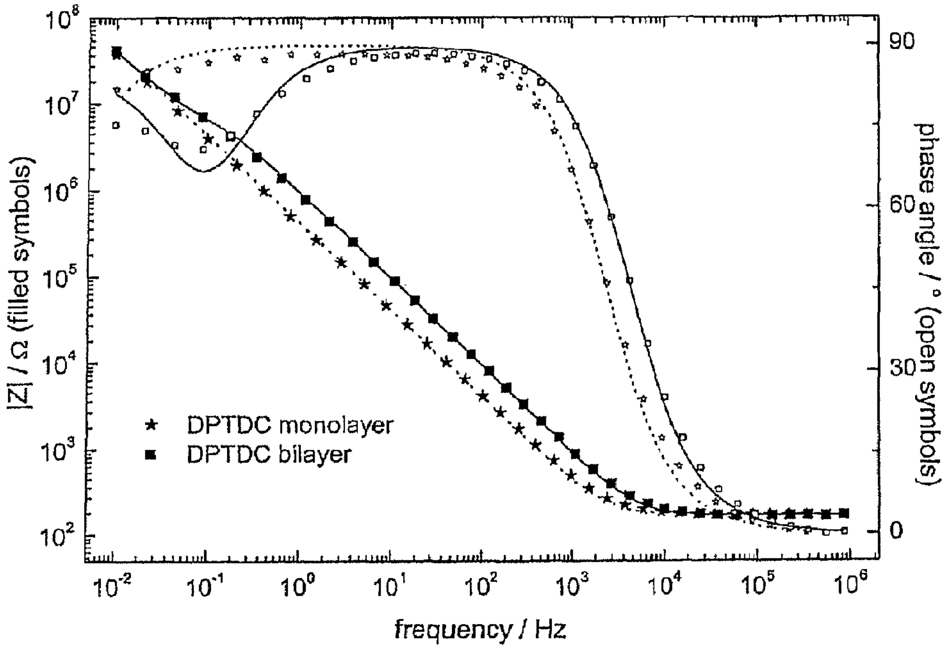
Figure 4B:
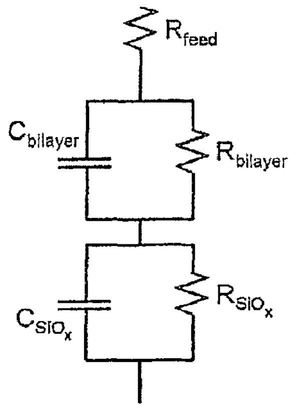

Bode plot of the EIS of a DPTDC monolayer (stars) and the same sample after one day of vesicle fusion (squares). Lines correspond to a fit using an equivalent circuit of a feed resistance in series with an RC element of the bilayer in series with an RC element of the SiOX layer (FIG. 4B). The fit to the measurement after vesicle fusion (bold line) yields: $R_{SiOx}$=26,7 MΩ, $C_{SiOx}$ =1,02 μF, $R_{bilayer}$=1,56 MΩ, $C_{bilayer}$=735 nF. Only one RC element representing the oxide layer with the attached SAM has been used to fit the substrate before vesicle fusion (dotted line): R=88,5 MΩ, C=987 nF.

FIG. 5

Bilayer growth during vesicle fusion as studied by ellipsometry. Circles represent the formation of a supported bilayer on a bare substrate, the squares show the bilayer formation on a substrate with a DPTTC monolayer. For both systems, Δ drops after insertion of the vesicles (0,1 mM DPhyPC 50 nm vesicles, cell filled with MilliQ water) at t=0 to a constant value after t ~30 min, whereas Ψ remain constant at ~18,3°.

FIG. 6

EIS of a bilayer and the effect of incorporated valinomycin at different $K^+/Na^+$ concentrations. FIG. 6A shows EIS data in a 100 mM NaCl buffer of a DPTDC covered substrate before vesicle fusion (circles), EIS in a 14 mM KCl/86 mM NaCl buffer after vesicle fusion and addition of 18 μM valinomycin in the cell (triangles up) and EIS of the same bilayer after thorough rinsing with 100 mM NaCl (triangles down). The line is a fit of an equivalent circuit (FIG. 4B). To focus on their differences, the lower part of FIG. 6A displays the same impedance data but normalized to the EIS before vesicle fusion. It can be seen that in the frequency range where the valinomycin acts (below ~10 Hz, triangles up) the impedance of the bilayer is strongly reduced, albeit not all the way down to the impedance of the monolayer.

Figure 6:
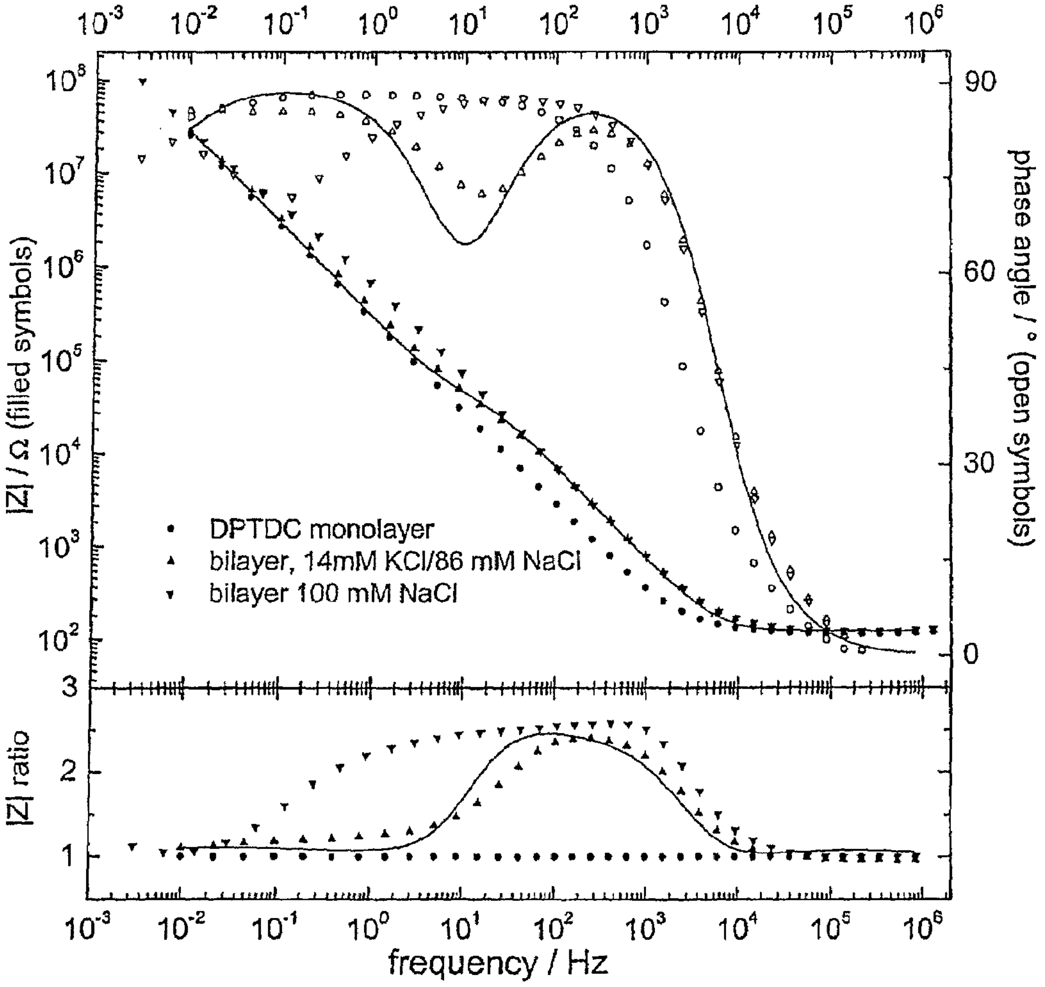
Figure 6B:
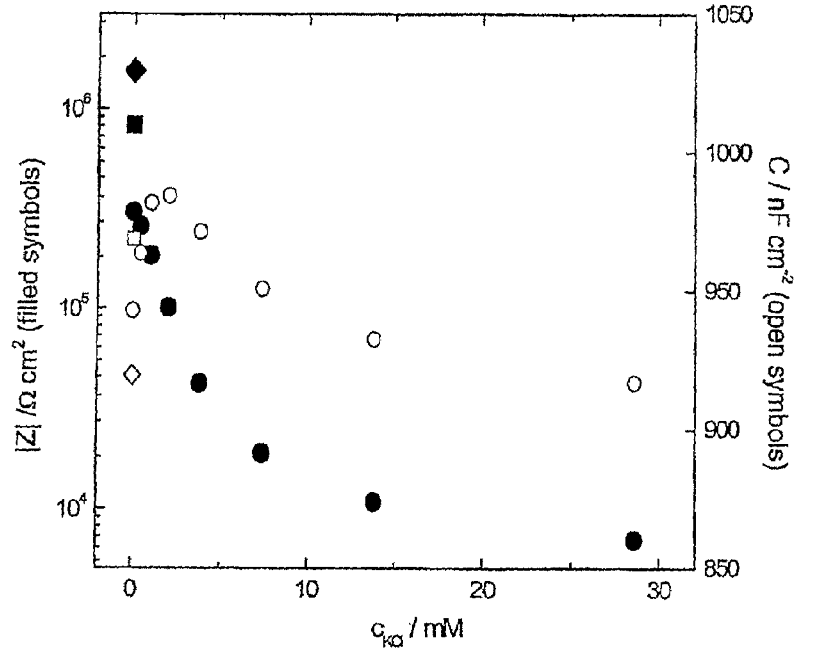

In FIG. 6B, the circles mark valinomycin incorporated bilayer resistances (●) and capacitance (○) from fits to EIS at different $K^+/Na^+$ ratios, but constant 100 mM ion strength. After a rapid drop, the bilayer resistance approaches a constant value of ~7 kΩ $cm^2$ for higher KCl concentrations. The bilayer resistance in 100 mM NaCl before valinomycin incorporation (■) is lower than after incorporation and rinsing with 100 mM NaCl (♦), what might be due to traces of $K^+$ ions left in the valinomycin. Whereas the resistance varies over two orders of magnitude, the capacitance stays in a narrow range.

FIG. 7

Figure 5:
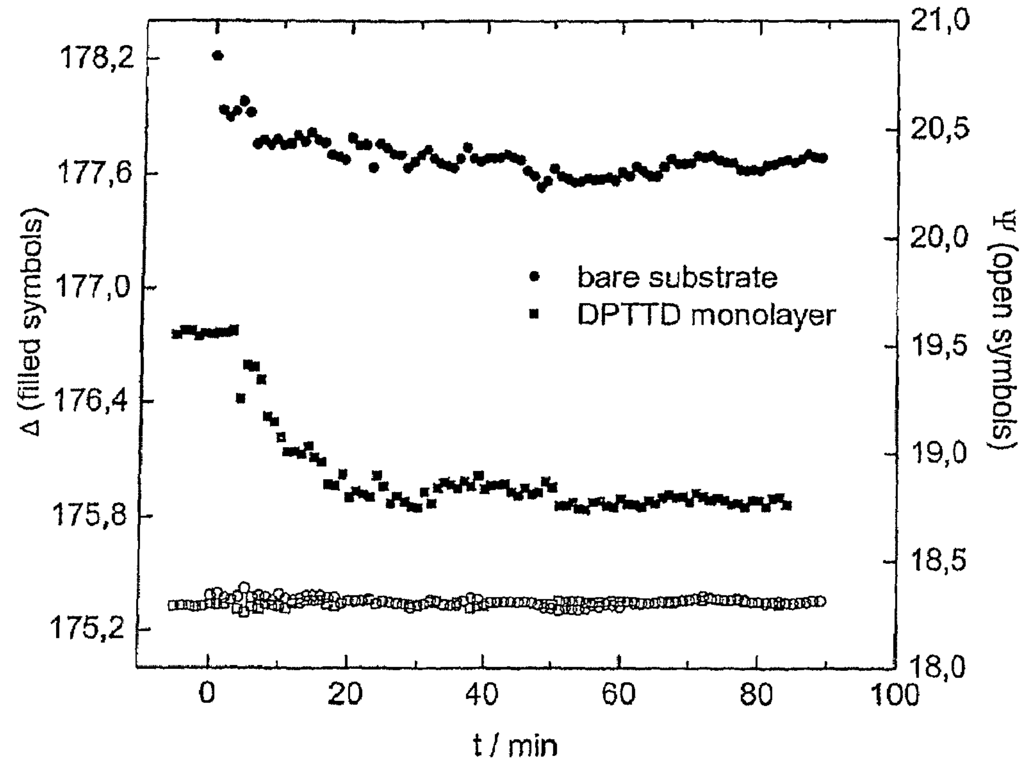
Figure 7:
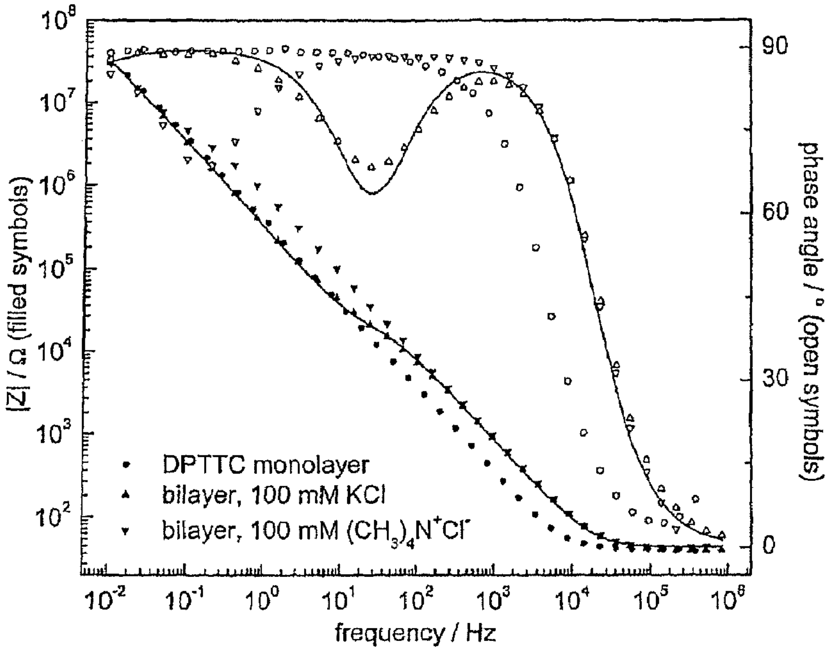
Figure 7:
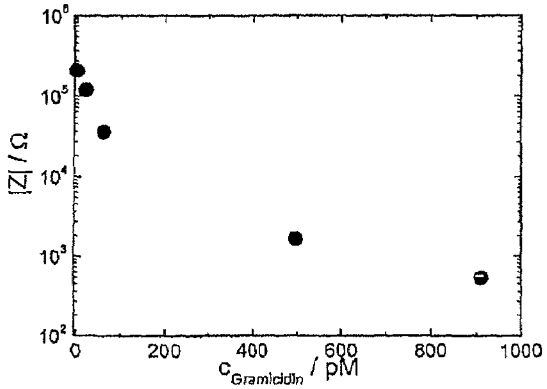

EIS of a tBLM and the effect of different ion size on the conductance of incorporated gramicidin channels. FIG. 7A shows EIS in a 100 mM KCl buffer of a DPTTC covered substrate before (circles) and after vesicle fusion (squares), EIS in a 100 mM KCl/410 pM gramicidin buffer of the same bilayer (triangles up) and EIS of the same bilayer after thorough rinsing with 100 mM tetramethylammoniumchloride (triangles down). The data can be described using an equivalent circuit (FIG. 5B). These fits yield in a bilayer resistance 540 kΩ $cm^2$, a reduced bilayer resistance of 13 kΩ $cm^2$ in the gramicidin buffer, and an increased bilayer resistance of 1.8 MΩ $cm^2$ after rinsing with tetramethylammoniumchloride. Only one fit (line) is shown for clarity reasons.

In FIG. 7B, resistances from of a different experiment from fits to EIS in 100 mM KCl are plotted for different gramicidin concentrations. Whereas the bilayer resistance varies over more than two orders of magnitude, the capacitance remains almost constant at ~780 nF $cm^{-2}$.

EXAMPLE

Synthesis and Immobilization of DPTTC and DPTDC

The tBLMs presented are based on two molecules: the archaeal analogue lipid 2,3-di-O-phytanyl-sn-glycerol-1-tetraethylene glycol-(3-trichloropropyl-silane) ether lipid (DPTTC) and 2,3-di-O-phytanyl-sn-glycerol-1-tetraethylene glycol-(3-chloro-dimethylpropyl-silane) ether lipid (DPTDC).

The basic synthetic route is depicted in Scheme 1. The lipids utilized have two phytanyl chains connected to the tetra(ethylene glycol) tethered spacer via a glycerol unit.

Phytanyl chains were chosen as hydrophobic tails instead of alkyl chains because of their low phase-transition temperature and their influence on the density and stability of biological membranes (Braach-Maksvytis and Raguse 2000; Raguse and others 2000). Furthermore, the 2,3-di-O-phytanyl-sn-glycerol unit contains only ether linkages to prevent hydrolytic cleavage (Mathai and others 2001).

The choice of the tethering moiety is based on the criteria it has to fulfill: it should be hydrophilic and should not interact either with membrane lipids or with membrane proteins. For the robustness required in practical applications, it should also be chemically linked to the bilayer at one end and to the solid substrate (silicon wafer) at the other end. Furthermore, it should not engage in extensive physical interactions with the surface. Tetra (ethylene glycol) is likely to fulfill these requirements—it is known to prevent nonspecific adsorption of proteins to surfaces (Du and others 1997; Lee and others 1995; Prime and Whitesides 1991), does not absorb to the Ipid bilayer surfaces (Arnold and others 1990), and interacts only minimally with quartz and glass surfaces (Ariga and others 1995).

DPTTC and DPTDC are immobilized on $SiO_x$ surfaces by immersing the substrate into a dilute (typically 2-40 mM) solution of either DPTTC or DPTDC in dry toluene. A few drops of dry $Et_3N$ are added to quench the co-product HCl and to promote the reaction (Kallury and others 1994; Tripp and Hair 1993). It should be emphasized that the difference between immobilization procedures of both lipids occurs within a thin water layer adsorbed to the substrate. This is required in the case of DPTTC.

Methods and materials

Chemicals (±)-3-Benzyloxy-1,2-propanediol 2, tetraethylene glycol 5 and allyl p-toluenesulfonate 6 (all purchased from Fluka) were dried over molecular sieve A3. Triethylamine (TEA, Acros) and THF (Fisher) were dried over $CaH_2$ and potassium, respectively. Trichlorosilane (Acros) and chlorodimethylsilane (Lancaster) were distilled prior to use. 1,2-Di-O-phytanoyl-sn-glycero-3-phosphocholine (DPhyPC) (Avanti Polar Lipids), valinomycin (Fluka), gramicidin D (*bacillus brevis*, Sigma), potassium chloride, sodium chloride, tetramethylammonium chloride (Acros), p-toluenesulfonyl chloride (TosCl, Acros), platinum on activated charcoal (Pt/C, Fluka), hexachloroplatinic acid ($H_2PtCl_6$, Fluka), sodium hydride (NaH, Aldrich) and toluene (Acros, water <30 ppm) were used as received.

Substrates

Highly p-doped silicon wafers (diameter 3", orientation <100>, boron-doped 0.005-0.002 Ωcm) were used to fabricate the electrolyte-insulator-semiconductor chips. The wafer was not further oxidized but retained the native oxide layer. The backside contact was made by evaporation of 250 nm aluminium followed by a temper step ($N_2$, 400° C., 10 min). Finally the wafers were cut into squares of 9 mm×9 mm to fit the experimental set-up.

Cleaning Procedure

Prior to use the Si wafers were cleaned thoroughly. A typical cleaning procedure was: ultrasonification (US) in pure water (MilliQ, R>18 MΩ cm) for 10 min, US in a 1:1 mixture of acetone:ethanol for 10 min, 300 W plasma-cleaning (0.9 mbar argon/0.1 mbar oxygen) for 5 min and US in MilliQ for 10 min. If necessary, the samples were stored in MilliQ. After such a cleaning procedure, the water contact angle was below 10°, the thickness of the oxide layer as determined by ellipsometry was 18±5 Å and the RMS-roughness determined by AFM was 2.0±0.5 Å (from a 5 μm×5 μm area, roughness from features smaller than 10 nm is probably not resolved by the AFM tip).

Electrochemical Impedance Spectroscopv (EIS)

EIS measurements were conducted using an IM6 spectrometer from Zahner Electrics. Spectra were recorded for frequencies between 10 mHz and 1 MHz at 0 V potential with an AC modulation amplitude of 10 mV. Raw data were analysed using the ZVIEW software package (Version 2.70, Scribner Associates). Standard three electrode measurements were performed in Teflon cells with the substrates as the working electrode, a coiled platinum wire as the counter electrode and a DRIREF-2 reference electrode (World Precision Instruments). The home-built Teflon cells have a buffer volume of 0.5 ml and an electrochemically open area on the substrates of 0.385 $cm^2$. The data was fitted using an equivalent circuit consisting of a feed resistance and two RC elements (a resistance connected in parallel to a capacitance) in series (FIG. 4B). The fitted values are normalized to the electrode surface area.

Atomic Force Microscopy (AFM)

The samples were scanned with a Dimension 3100 model (Veeco, Santa Barbara, Calif.) under ambient conditions. Single beam silicon cantilevers (Olympus OMCL-AC160TS-W2 TappingMode) with spring constants of ~45 N/m and resonant frequencies of ~300 kHz have been used. The roughness is determined from topographs recorded in tapping mode.

Ellipsometry

Ellipsometric measurements were carried out using an $EP^3$ imaging ellipsometer from Nanofilm with a λ=532 nm laser source. The angle of incidence was 70° for measurements in air, 60° for measurements in a fluid cell. Thickness values were fitted with the $EP^3$View V2.01 software using a layer model with the following parameters: n=4.17 and k=0.049 for Si, n=1.4605 and k=0 for $SiO_x$, n=1.50 and k=0 for the self-assembled monolayers (SAM), and n=1.45 and k=0 for the bilayer (Naumann and others 2003a). SAM thicknesses were determined by comparing results before and after the growth of layer.

Immobilization of DPTDC on $SiO_x$ Surfaces (SAM Preparation).

DPTDC was immobilized on the $SiO_x$ surface of a silicon wafer at room temperature from toluene solutions using $Et_3N$ as promoter and acid scavenger. The substrates were dried by vacuum firing and immerged in an assembly solution. The SAMs were typically assembled within 24 h. The samples were then cleaned by rinsing extensively and ultrasonified 5 min in toluene, toluene:ethanol=1:1 and ethanol, followed by rinsing with chloroform.

Immobilization of DPTTC on $SiO_x$ Surfaces (SAM Preparation).

The procedure is essentially the same as for DPTDC, except that the silicon wafers were not dried prior to assembly (a water layer on the substrate surface is required).

Vesicle Fusion (tBLM and sBLM Preparation)

Bilayers were grown on the substrates by insertion of 0,2 mM DPhyPC (1,2-Diphytanoyl-sn-glycero-3-phosphocholine) vesicles (50 nm Ø by extrusion in MilliQ) into the electrochemical cells with a buffer of typically 100 mM KCl. For tBLM preparations, substrates previously treated with DPTDC and DPTTC were used. Supported bilayer lipid membranes (sBLM) were assembled by using cleaned but untreated substrates where the vesicles directly interact with the hydrophilic silicon oxide layer.

Incorporation of Valinomycin and Gramicidin

Valinomycin and gramicidin were dissolved in ethanol (2 mg/ml and 5 ng/ml respectively) and added to the preformed bilayer. Incorporation was allowed for one hour. The final concentration of valinomycin in the cell was 18 μM, the concentration of gramicidin was varied as described below between 20 and 1000 nM.

Immobilization of DPTDC and DPTTC on $SiO_x$ Surfaces

Figure 2:
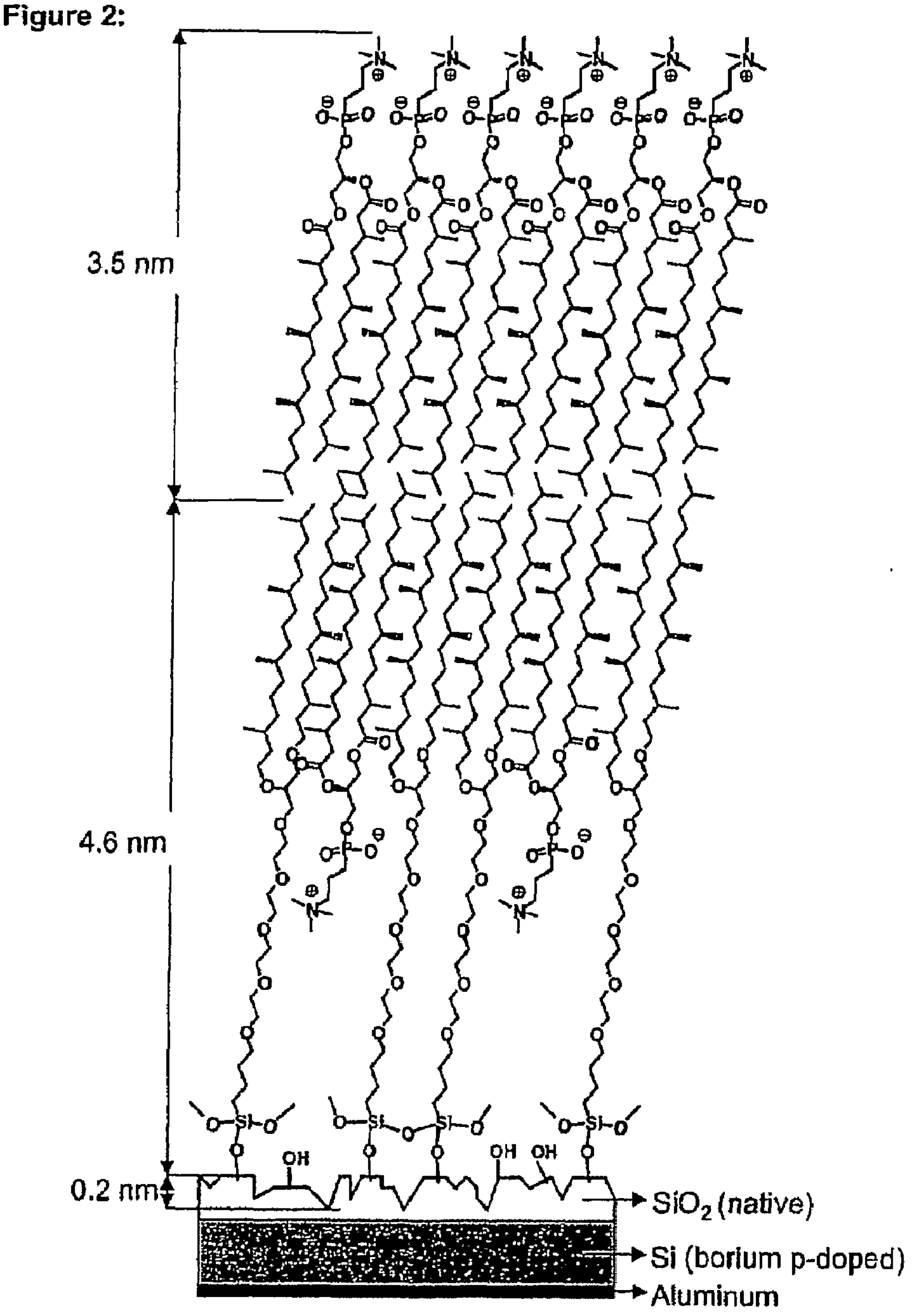

Substrates treated with DPTDC and DPTTC for one day as described above have advancing water contact angles of 86°±4° and 91°±5° respectively and receding water contact angles of 59°±3° and 66°±4° respectively. The time scale of the immobilisation can be seen in FIG. 3. Average thickness of the SAM as determined by ellipsometry are 1,3 nm±0,5 nm for DPTDC and 1,8 nm±0,6 nm for DPTTC, which has to be compared to the calculated molecular length of 4,6 nm (FIG. 2). AFM topographs show a slightly rougher surface of the substrate than before deposition of the monolayer, but the film is homogeneous and no structures like islands can be observed (AFM data not shown). EIS of the samples before and after immobilization showed a ~20% decrease of the capacitance of the oxide layer due to the additional thickness of the SAM.

From the strong increase of the contact angle it is suggested that a thin first layer of molecules is bound to the silicon oxide surface. The molecules, however, are not closely packed to form a densely packed monolayer but seem to form a rather diluted film, which can be presumed from the undersized film thickness as determined by ellipsometry as well as from the difference between advancing and receding contact angles.

Growth and Electrochemical Properties of the Lipid Bilayer

Impedance spectra of the substrates with an attached SAM can be analyzed by an equivalent electrical circuit consisting of a feed resistance and an RC element (a resistance connected in parallel to a capacitance) describing the oxide/SAM layer. After vesicle insertion, a second RC element forms within a few hours with a rapid drop in capacitance and a steady increase in resistance. The bilayer formation is usually completed within 24 h as determined from a saturation of the bilayer resistance. The two RC elements corresponding to the oxide layer and the tethered bilayer can be easily distinguished in the combined impedance and phase Bode plot shown in FIG. 4A. The logarithm of the absolute value of the impedance (left ordinate) and the phase angle (non logarithmic, right ordinate) are plotted versus the logarithmic AC modulation frequency. In such a log-log plot, resistively dominated frequency regions are horizontal with zero phase and capacitive dominated frequency regions have a slope of minus one and are out of phase by 90°, with higher capacitance shifting the curve to lower frequencies. Accordingly, the measurement after bilayer growth reveals a flat impedance with low phase at high frequencies (>10 kHz) where the solution resistance dominates the current response, a rising impedance of slope minus one and out of phase in the broad mid-frequency region where the capacitance of the oxide layer and the bilayer in series dominate, and the low frequency region (<0.1 Hz) where only the capacitance of the oxide layer persists. The last two regions are separated by a transition shoulder region with lower phase which manifests the resistance of the bilayer. The data can be fitted with good agreement using the equivalent circuit shown in FIG. 4B.

The average bilayer resistances and capacitances, determined from 10 different samples, are 1.45±1.06 MΩ $cm^2$ and 888±36 nF $cm^{-2}$ for DPTDC, and 0.5±0.3 MΩ $cm^2$ and 782±26 nF $cm^{-2}$ for DPTTC respectively. The bilayers are stable over more than a week and are robust upon rinsing. Compared to supported bilayers, where bilayer resistances were usually lower by more that one order of magnitude, the relatively high bilayer resistances of about 1 MΩ $cm^2$ in case of the tBLM architectures suggest a partial filling of the lightly packed proximal bilayer leaflet by lipids from the vesicles.

Figure 3:
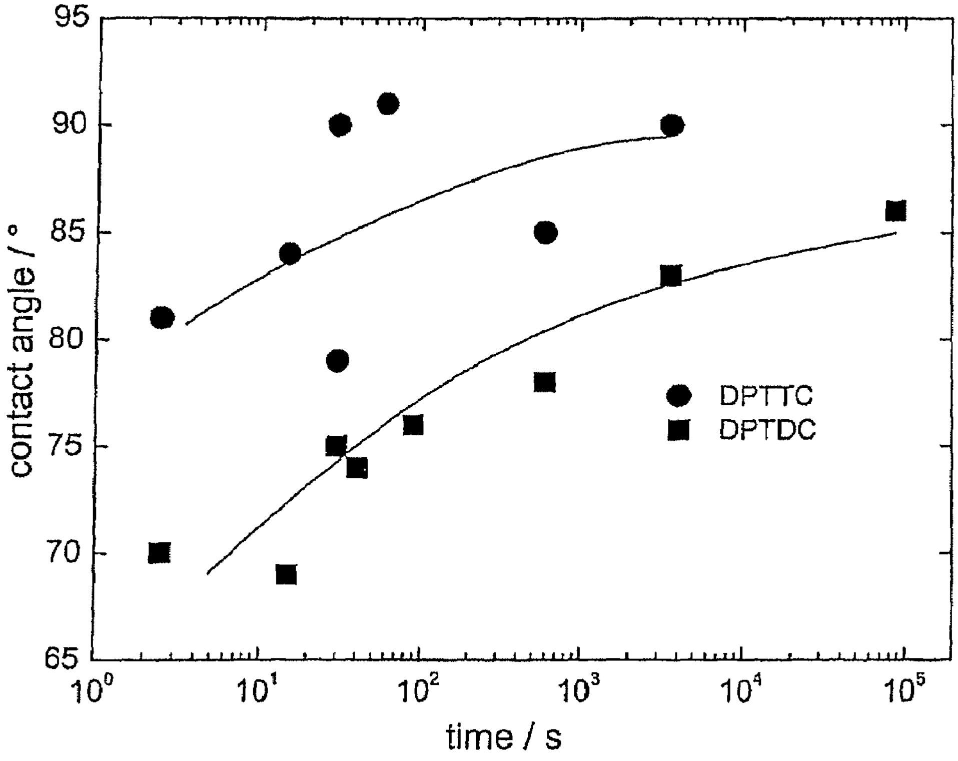

The difference between the two systems (DPTDC and DPTTC) can be explained with a different monolayer structure or packing density as can be seen from the different hydrophobic character of the surface (FIG. 3). However, both systems show reasonably good electrical sealing properties to be used as a biomimetic membrane.

The kinetics of the bilayer formation were studied by ellipsometry using a liquid cell filled with MilliQ water. The growth of the bilayer after vesicle insertion on a bare substrate and on a DPTTC covered substrate can be compared in FIG. 4. The drop in Delta is more pronounced for the SAM covered sample corresponding to an overall thicker bilayer system. A simple layer model assuming a constant refractive index of n=1.45 for the whole bilayer system yields a bilayer thickness of about 2 nm for the supported bilayer and about 4 nm for the tethered bilayer. These bilayer thicknesses are too low compared to the calculated lengths of the molecules involved in the bilayer formation (FIG. 2). This might be due to shortcomings of the model and difficulties in the measurement because of proximate refractive indices of the different layers (n=1.4605 for $SiO_x$, n=1.45 for the bilayer and n=1.33 for water).

Incorroration of Proteins

The first test on functionality of the membrane was the addition of valinomycin, a small ion carrier peptide. Valinomycin spontaneously partitions into the membrane and selectively transports $K^+$ ions from one side to the other (Peggion and others 2001; Raguse and others 1998). Thus, one can expect a strong decrease in the bilayer membrane resistance with an increasing potassium ion concentration in case the protein is functionally incorporated.

FIG. 6 shows the EIS data from a DPTDC-based tBLM with incorporated valinomycin using buffer solution of different compositions of $Na^+$ and $K^+$ ions at an ionic strength of 100 mM. FIG. 6A compares Bode plots (●) before vesicle fusion, (▲) after vesicle fusion, valinomycin incorporation and in a mixed KCl/NaCl buffer and (▼) after rinsing with a pure NaCl buffer. To better visualize the difference in the bilayer impedance, we have replotted the curves by normalizing them to the curve before vesicle fusion (lower part of FIG. 6A). This procedure yields the ratios of the impedances of the different curves. It can be seen, that the brayer increases the impedance by a factor of 2.5 in the mid-frequency region. For the bilayer with the active Valinomycin, this factor is reduced again to only 1.25 at lower frequencies. The data can be approximately fitted using the simple R—RC—RC equivalent circuit as discussed above. The obtained values for the bilayer resistances and capacitances from different potassium ion strengths are plotted in FIG. 6B.

With increasing potassium concentration the resistance of the bilayer decreases as expected, first rapidly then slower until it approaches for higher potassium concentrations asymptotically a small fraction of the original bilayer resistance. At the same time, the membrane capacitance remains almost constant. After rinsing with 100 mM NaCl solution, the membrane resistance increases again.

As a control, electrolyte solutions with different NaCl/KCl concentrations at 100 mM ionic strength show no significant effect on the electrical properties of a protein-free bilayer.

As a second test on the functionality of the membrane, we incorporated gramicidin into the bilayer. Gramicidin is a polypeptide with alternating D and L amino acids. In lipid bilayer membranes, gramicidin dimerizes and folds as a right handed β-helix to form an ion channel that just spans the bilayer (Andersen and others 1999; Langs 1988). Whereas $K^+$ and $Na^+$ ions penetrate the channel, other ions like the bigger tetramethylammonium ($(CH_3)_4N^+$) or ammonium ($NH_4^+$) ions are excluded (Sancho 1997). This effect has been already proposed to be used in a biosensing concept (Cornell and others 1997; Hirano and others 2003; Nikolelis and Siontorou 1996). However, most of the approaches are based on black lipid membranes that lack mechanical stability. Supported systems, on the other hand, do not give highly insulating membranes. According to the invention it is possible to combine the stability of a tethered membrane with a highly insulating bilayer, which can be used for biosensing applications on semiconductor chips.

FIG. 7A shows the Bode plot for a bilayer build on a DPTTC monolayer in 100 mM KCl before and after addition of gramicidin to the buffer and after rinsing with tetramethylammoniumchloride solution. The data are fitted using the same approach as above. The decrease of the bilayer resistance from 540 kΩ $cm^2$ to 13 kΩ $cm^2$ can be attributed to the incorporation of the gramicidin channels. This interpretation is affirmed by the strong increase of the bilayer resistance to 1.8 MkΩ $cm^2$ after rinsing with tetramethylammoniumchloride solution. This resistance is even higher than the original bilayer resistance in KCl solution before gramicidin incorporation. This shows the influence of the different ion sizes and mobilities on the bilayer resistance. In control experiments, it is found that membrane resistances in tetramethylammonium-chloride solution increase by a factor of about two with respect to membranes in KCl solutions. The changes due to gramicidin incorporation are thus much more pronounced.

The obtained values for the bilayer resistance as a function of the gramicidin concentration are plotted in FIG. 7B. A strong drop of the bilayer resistance by more than two orders of magnitude can be observed when the concentration of the ion channel is increased up to about 1000 pM. At the same time, the bilayer capacitance is constant at 780 $nFcm^{-2}$. For gramicidin concentrations below 500 pM, this drop in the bilayer resistance can be reversed by rinsing with a 100 mM $(CH_3)_4N^+Cl^-$ buffer. For higher gramicidin concentrations, the bilayer resistance is reduced further until complete disappearance; also the initial bilayer resistance can no longer be regained by exchanging the buffer. This phenomenon could be due to permanent perturbation of the bilayer caused by a large amount of integrated protein molecules.

The invention claimed is:

1. Compounds of the general formulae (Ia) or (Ib)

(1a)

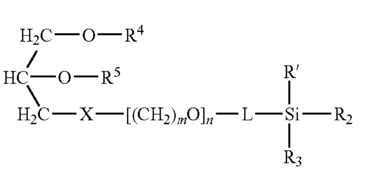

(1b)

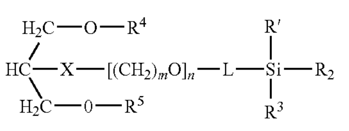

in which $R^1$, $R^2$ and $R^3$ are independently selected from the group consisting of saturated or unsaturated, branched or unbranched, susbtituted or unsubstituted C1 to C10 hydrocarbons, —Br, —CI, —$OR^6$, alkylsilanes, arylsilanes, silicoles and siloxanes, wherein at least one of $R^1$, $R^2$ and $R^3$ is selected from the group consisting of —Br, —CI, —$OR^6$ and wherein $R^6$ is a saturated or unsaturated, substituted or unsubstituted C1 to C10 hydrocarbon, and at least one of $R^4$ and $R^5$ independently denotes a saturated or unsaturated hydrocarbon residue or an acyl residue having a chain length of 10-22 C atoms which can optionally be substituted by one or several side groups and/or labelling groups, in particular fluorescent groups, and if only one of $R^4$ and $R^5$ denotes a residue as defined above the other is hydrogen, a $C_1$-$C_9$ hydrocarbon residue or a residue comprising a phospholipid, carboxyl, carbonyl, $SO_1$, $SO_2$, amide, amino or thiol group with or without a $C_1$-$C_9$ hydrocarbon residue, and n and m are independently integers ≧1, and L is a linker group selected from the group consisting of saturated or unsaturated, branched or unbranched, substituted or unsubstituted hydrocarbons having ≧1 C atoms, alkylsilanes, arylsilanes and siloxanes, and X is a connecting group.

2. Compounds as claimed in 1, characterized in that the —$SiR^1R^2R^3$ group is selected from chlorosilanes and alkoxyl silanes.

3. Compounds as claimed in claim 1, characterized in that the —$SiR^1R^2R^3$ group is selected from the group consisting of —$SiCI_3$, —$SiR^7Cl_2$, —$SiR^7{}_2CI$, —$Si(OR^6)_3$, $SiR^7{}_2(OR^6)$ and $Sir^7(OR^6)_2$, and $R^6$ and $R^7$ are independently saturated or unsaturated, branched or unbranched, substituted or unsubstituted C1 to C10 hydrocarbons.

4. Compounds as claimed in claim 1, characterized in that $R^6$ is $CH_3$ or $(CH_2)_pCH_3$ with p being an integer from 1 to 9.

5. Compounds as claimed in claim 1, characterized in that at least one of $R^4$ and $R^5$ is selected from saturated and unsaturated hydrocarbon residues.

6. Compounds as claimed in claim 5, characterized in that at least one of $R^4$ and $R^5$ is selected from saturated hydrocarbon residues which are substituted by one or more methyl groups.

7. Compounds as claimed in 1, characterized in that X represents O.

8. Compounds as claimed in 1, characterized in that n and m are independently integers from 1-20.

9. Compounds as claimed in 1, characterized in that n is an integer from 2-10.

10. Compounds as claimed in 1, characterized in that m is 2.

11. Compounds as claimed in 1, characterized in that they are selected from 2,3-di-O-phytanyl-sn-glycero-1-tetraethylene glycol-(3-trichioropropyl-silane) ether lipid, 2,3-di-O-phytanoyl-snglycero- 1-tetraethylene glycol-(3-chloro-dimethylpropyl-silane) ether lipid, corresponding 1,2- or 1,3-diphytanyl or diphytanoyl derivatives and optical isomers thereof.

* * * * *